(12) United States Patent
Qiao et al.

(10) Patent No.: US 11,644,470 B2
(45) Date of Patent: May 9, 2023

(54) SYSTEMS AND METHODS FOR DE NOVO PEPTIDE SEQUENCING USING DEEP LEARNING AND SPECTRUM PAIRS

(71) Applicant: BIOINFORMATICS SOLUTIONS INC., Waterloo (CA)

(72) Inventors: Rui Qiao, Waterloo (CA); Ngoc Hieu Tran, Waterloo (CA); Lei Xin, Waterloo (CA); Xin Chen, Waterloo (CA); Baozhen Shan, Waterloo (CA); Ali Ghodsi, Waterloo (CA); Ming Li, Waterloo (CA)

(73) Assignee: BIOINFORMATICS SOLUTIONS INC., Waterloo (CA)

( * ) Notice: Subject to any disclaimer, the term of this patent is extended or adjusted under 35 U.S.C. 154(b) by 428 days.

(21) Appl. No.: 16/846,817

(22) Filed: Apr. 13, 2020

(65) Prior Publication Data
US 2020/0326348 A1    Oct. 15, 2020

Related U.S. Application Data

(60) Provisional application No. 62/833,959, filed on Apr. 15, 2019.

(51) Int. Cl.
| | |
|---|---|
| *G01N 33/00* | (2006.01) |
| *G01N 33/68* | (2006.01) |
| *G16B 40/00* | (2019.01) |
| *G16B 20/00* | (2019.01) |
| *G16B 30/00* | (2019.01) |

(52) U.S. Cl.
CPC ......... *G01N 33/6848* (2013.01); *G16B 20/00* (2019.02); *G16B 30/00* (2019.02); *G16B 40/00* (2019.02)

(58) Field of Classification Search
None
See application file for complete search history.

(56) References Cited

U.S. PATENT DOCUMENTS

| | | | | |
|---|---|---|---|---|
| 2019/0018019 | A1* | 1/2019 | Shan | G06F 17/16 |
| 2019/0147983 | A1* | 5/2019 | Shan | G06N 3/02 |
| | | | | 702/20 |
| 2020/0243164 | A1* | 7/2020 | Qiao | G16B 25/10 |
| 2020/0372973 | A1* | 11/2020 | Serie | G16B 40/20 |
| 2022/0036973 | A1* | 2/2022 | Meller | G16B 40/20 |

(Continued)

OTHER PUBLICATIONS

Ngoc Hieu Tran, M Ziaur Rahman, Lin He, Lei Xin, Baozhen Shan, and Ming Li. Complete de novo assembly of monoclonal antibody sequences. Scientific reports, 6:31730, 2016.

(Continued)

*Primary Examiner* — Farhan M Syed
(74) *Attorney, Agent, or Firm* — Norton Rose Fulbright Canada LLP

(57) ABSTRACT

The present systems and methods are directed to de novo identification of peptide sequences from tandem mass spectrometry data. The systems and methods uses unconverted mass spectrometry data from which features are extracted. Using unconverted mass spectrometry data reduces the loss of information and provides more accurate sequencing of peptides. The systems and methods combine deep learning and neural networks to sequencing of peptides.

26 Claims, 5 Drawing Sheets

(56) References Cited

U.S. PATENT DOCUMENTS

2022/0154281 A1* 5/2022 Boucher .............. G06N 3/0454

OTHER PUBLICATIONS

Ngoc Hieu Tran, Rui Qiao, Lei Xin, Xin Chen, Chuyi Liu, Xianglilan Zhang, Baozhen Shan, Ali Ghodsi, and Ming Li. Deep learning enables de novo peptide sequencing from data-independent-acquisition mass spectrometry. Nature methods, 16(1):63-66, 2019.

Vlado Dancík, Theresa A Addona, Karl R Clauser, James E Vath, and Pavel A Pevzner. De novo peptide sequencing via tandem mass spectrometry. Journal of computational biology, 6(3-4):327-342, 1999.

J Alex Taylor and Richard S Johnson. Implementation and uses of automated de novo peptide sequencing by tandem mass spectrometry. Analytical chemistry, 73(11):2594-2604, 2001.

Bin Ma, Kaizhong Zhang, Christopher Hendrie, Chengzhi Liang, Ming Li, Amanda Doherty-Kirby, and Gilles Lajoie. Peaks: powerful software for peptide de novo sequencing by tandem mass spectrometry. Rapid communications in mass spectrometry, 17(20):2337-2342, 2003.

Ari Frank and Pavel Pevzner. Pepnovo: de novo peptide sequencing via probabilistic network modeling. Analytical chemistry, 77(4):964-973, 2005.

Bernd Fischer, Volker Roth, Franz Roos, Jonas Grossmann, Sacha Baginsky, Peter Widmayer, Wilhelm Gruissem, and Joachim M Buhmann. Novohmm: a hidden markov model for de novo peptide sequencing. Analytical chemistry, 77(22):7265-7273, 2005.

Ngoc Hieu Tran, Xianglilan Zhang, Lei Xin, Baozhen Shan, and Ming Li. De novo peptide sequencing by deep learning. Proceedings of the National Academy of Sciences, 114(31):8247-8252, 2017.

Kelvin Xu, Jimmy Ba, Ryan Kiras, Kyunghyun Cho, Aaron Courville, Ruslan Salakhudinov, Rich Zemel, and Yoshua Bengio. Show, attend and tell: Neural image caption generation with visual attention. In International conference on machine learning, pp. 2048-2057, 2015.

Karen Simonyan and Andrew Zisserman. Very deep convolutional networks for large-scale image recognition. arXiv preprint arXiv:1409.1556, 2014.

Joseph Redmon, Santosh Divvala, Ross Girshick, and Ali Farhadi. You only look once: Unified, real-time object detection. In Proceedings of the IEEE conference on computer vision and pattern recognition, pp. 779-788, 2016.

Yoon Kim. Convolutional neural networks for sentence classification. arXiv preprint arXiv:1408.5882, 2014.

Tsung-Yi Lin, Priya Goyal, Ross Girshick, Kaiming He, and Piotr Dollár. Focal loss for dense object detection. In Proceedings of the IEEE international conference on computer vision, pp. 2980-2988, 2017.

Abadi, M. et al., Tensorflow: A system for large-scale machine learning. In 12th USENIX Symposium on Operating Systems Design and Implementation (OSDI16), pp. 265-283, 2016.

Adam Paszke, Sam Gross, Soumith Chintala, Gregory Chanan, Edward Yang, Zachary DeVito, Zeming Lin, Alban Desmaison, Luca Antiga, and Adam Lerer Automatic differentiation in pytorch. In NIPS-W, 2017.

Charles R Qi, Hao Su, Kaichun Mo, and Leonidas J Guibas. Pointnet: Deep learning on point sets for 3d classification and segmentation. In Proceedings of the IEEE Conference on Computer Vision and Pattern Recognition, pp. 652-660, 2017.

Ashish Vaswani, Noam Shazeer, Niki Parmar, Jakob Uszkoreit, Llion Jones, Aidan N Gomez, Łukasz Kaiser, and Illia Polosukhin. Attention is all you need. In Advances in Neural Information Processing Systems, pp. 5998-6008, 2017.

Diederik P Kingma and Jimmy Ba. Adam: A method for stochastic optimization. arXiv preprint arXiv:1412.6980, 2014.

* cited by examiner

SYSTEMS AND METHODS FOR DE NOVO PEPTIDE SEQUENCING USING DEEP LEARNING AND SPECTRUM PAIRS

CROSS REFERENCE TO RELATED APPLICATION

This application claims the benefit of U.S. provisional application No. 62/833,959, titled "Systems and Methods for De Novo Peptide Sequencing Using Deep Learning and Spectrum Pairs", filed on Apr. 15, 2019, the entire content of which is incorporated herein by reference.

FIELD OF THE INVENTION

The invention relates to the field of protein sequencing and, more specifically, de novo peptide sequencing using deep learning.

BACKGROUND OF THE INVENTION

Proteomics research focuses on large-scale studies to characterize the proteome, the entire set of proteins, in a living organism. In proteomics, de novo peptide sequencing from tandem mass spectrometry (MS/MS) data plays the key role in the characterization of novel protein sequences. This field has been studied over the past 20 years and a number of de novo sequencing tools have been proposed such as PepNovo™, PEAKS™, NovoHMM™, MSNovo™, pNOVO™, UniNOVO™, Novor™ among others. However, computational challenges still remain as MS/MS spectra contain a significant level of noise and ambiguity.

SUMMARY OF THE INVENTION

In accordance with an aspect of the present invention, there is provided a computer implemented system for de novo sequencing of peptides from a sample mass spectrometry data using neural networks, the computer implemented system comprising: a processor and at least one memory providing a plurality of layered nodes configured to form an artificial neural network for generating a probability measure for one or more candidates to a next amino acid in an amino acid sequence, the artificial neural network trained on known mass spectrometry data representing theoretical fragment ions peaks of known sequences differing in length and differing by one or more amino acids; wherein the plurality of layered nodes comprise at least one node configured to receive: the sample mass spectrometry data comprising a plurality of coordinate data pairs representing m/z and intensity values of observed fragment ion peaks, and a second coordinate data representing the theoretical fragment ion peaks; wherein the plurality of layered nodes receives the sample mass spectrometry data as input, the plurality of layered nodes comprising: at least one convolutional and/or fully connected layer for comparing at least one of the observed fragment ion peak against at least one of the theoretical fragment ion peaks; and the processor configured to: obtain an input prefix representing a determined amino acid sequence of the peptide, identify a next amino acid based on a candidate next amino acid having a greatest probability measure based on the output of the artificial neural network and the sample mass spectrometry data; and update the determined amino acid sequence with the next amino acid.

In another aspect, there is provided a method for de novo sequencing of peptides from mass spectrometry data using a plurality of layered nodes configured to form an artificial neural network for generating a probability measure for one or more candidates to a next amino acid in an amino acid sequence, the method comprising: receiving, by at least one node of the plurality of layered nodes, a sample mass spectrometry data of a sample peptide, the sample mass spectrometry data comprising a plurality of coordinate data pairs representing m/z and intensity values of observed fragment ion peaks; receiving, by the at least one node, a second coordinate data representing theoretical fragment ion peaks; comparing at least one of the observed fragment ion peak against at least one of the theoretical fragment ion peaks, by at least one convolutional and/or fully connected layer of the plurality of layered nodes; obtaining an input prefix representing a determined amino acid sequence of the sample peptide; outputting a probability measure for each candidate of a next amino acid; identifying a next amino acid based on a candidate next amino acid having a greatest probability measure based on the output of the artificial neural network and the sample mass spectrometry data; and updating the determined amino acid sequence with the next amino acid.

BRIEF DESCRIPTION OF THE FIGURES

Embodiments of the invention may best be understood by referring to the following description and accompanying drawings. In the drawings.

DETAILED DESCRIPTION

Figure 1:
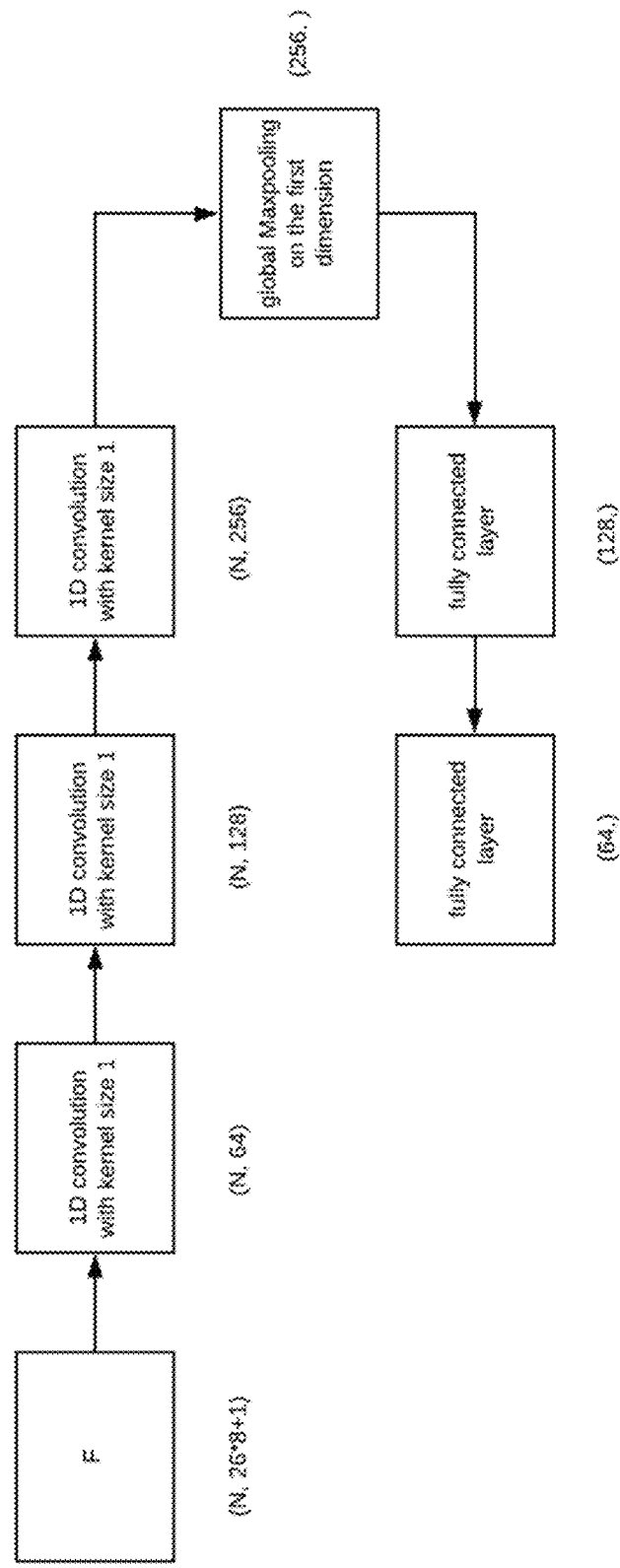
FIG. 1 shows a flow chart of the architecture of T Net. F represents extracted Feature matrix. N refers to the number of fragment ion peaks.

In proteomics, De novo peptide sequencing from tandem Mass Spectrometry (MS) data is the key technology for finding new peptide or protein sequences. It has successful applications in assembling monocolonal antibody sequences (mAbs) [1] and great potentials in identifying neoantigens for personalized cancer vaccines [2]. Given the importance of the de novo peptide sequencing technology, massive research have been done in this area and different tools have been proposed[3][4][5][6][7]. Tran et al. (2017) first introduced deep learning to de novo peptide sequencing and proposed DeepNovo, a neural network based de novo peptide sequencing model[8] for Data Dependent Acquisition (DDA) of MS data (see also US Patent Publication No. 20190018019, the entire contents of which is incorporated herein by reference). In DeepNovo, each spectrum is represented as a long intensity vector and convolutional neural networks (CNN) are applied on segments of this vector to extract features and make predictions of the next amino acid.

Tran et al. (2019) further extended DeepNovo on Data Independent Acquisition (DIA) MS data and proposed DeepNovo-DIA [2], the first de novo peptide sequencing algorithm for DIA MS/MS spectrums (see also U.S. application Ser. No. 16/226,575, the entire contents of which is incorporated herein by reference). Comparing to DDA, DIA data are in general harder to interpret because the spectrum generated by DIA often contains multiple peptides' fragment ions. On the other hand, the multiplexity and noise in the DIA spectrums make deep neural networks a more reasonable choice. In DeepNovo-DIA, each detected feature is represented by 5 spectrums, where each spectrum is discretized into an intensity vector as in DeepNovo. accuracy [2].

Presently, further developments have been made to provide systems and methods for de novo peptide sequencing of peptides from mass spectrometry data, using improved MS data representation, input data format, and feature extraction model.

As used herein, "de novo peptide sequencing" refers to a method in which a peptide amino acid sequence is determined from raw mass spectrometry data. De novo sequencing is an assignment of peptide fragment ions from a mass spectrum. In a mass spectrum, an amino acid is determined by two fragment ions having a mass difference that corresponds to an amino acid. This mass difference is represented by the distance between two fragment ion peaks in a mass spectrum, which approximately equals the mass of the amino acid. In some embodiments, de novo sequencing systems apply various forms of dynamic programming approaches to select fragment ions and predict the amino acids. The dynamic programming approaches also take into account constrains, for example that a predicted amino acid sequence must have corresponding mass.

As used herein, "deep learning" refers to the application to learning tasks of artificial neural networks (ANNs) that contain more than one hidden layer. Deep learning is part of a broader family of machine learning methods based on learning data representations, as opposed to task specific algorithms. One key aspect of deep learning is its ability to learn multiple levels of representation of high-dimensional data through its many layers of neurons. Furthermore, unlike traditional machine learning methods, those feature layers are not pre-designed based on domain-specific knowledge and hence they have more flexibility to discover complex structures of the data.

In one embodiment, a deep learning system is provided for de novo peptide sequencing. The system combines a prediction neural network for order invariant date, and a recurrent neural network (RNN) to learn features of tandem mass spectra, fragment ions, and sequence patterns of peptides based on a language model.

Mass Spectrometry

In some embodiments, the system comprises a mass spectrometer, examples of which include: tandem mass spectrometer (MS/MS) and liquid chromatography tandem mass spectrometer (LC-MS/MS). LC-MS/MS combines liquid chromatography (LC) with a tandem mass spectrometer. Mass spectrometry (MS) is an analytical technique that ionizes chemical species and sorts the ions based on their mass-to-charge ratio. A tandem mass spectrometer (MS/MS) involves two stages of mass spectrometry selection and fragmentation. MS can be applied to pure samples as well as complex mixtures. In an example MS procedure, a sample, which may be solid, liquid, or gas, is ionized, for example, by bombarding it with electrons. This causes some of the sample's molecules to break into charged fragments of various sizes and masses.

For example, a 10 amino acid length polypeptide is fragmented between the $3^{rd}$ and $4^{th}$ amino acid, resulting in one fragment of 3 amino acids long and another fragment of 7 amino acids long. These are also referred to as b- and y-ions. A 10 amino acid length polypeptide can also be fragmented between the central carbon (alpha-carbon) of an amino acid residue and it' respective carbonyl carbon (C=O). These ions are then separated according to their mass-to-charge ratio and detected. The detected ions are displayed as a mass spectra of the relative abundance of detected ions as a function of the mass-to-charge ratio.

As used herein, "b-ion" and "y-ion" refer to peptide fragments or fragment peaks on tandem mass spectrum resulting from fragmenting a polypeptide at the peptide bond. The b-ion extends from the amino terminus of the fragmented peptide, while y-ion extends from the C-terminus of the fragmented peptide. A mass spectrum contains fragment peaks corresponding to b- and/or y-ions that vary by one or more amino acid residues. In some embodiments, determining peptide sequences from the amino terminus of the peptide is referred to as the forward direction, while determining peptide sequences from the C-terminus of the peptide is referred to as the backward direction.

As used herein, an "a-ion" refers to peptide fragments or fragment peaks on tandem mass spectrum resulting from fragmenting a polypeptide at the central carbon (alpha-carbon) of an amino acid residue and it' respective carbonyl carbon (C=O). A mass spectrum contains fragment peaks corresponding to b-ions that vary by one or more amino acid residues. An a-ion differs from a corresponding b-ion by an carbonyl group (C=O) and their corresponding fragment peaks in a mass spectrum are separated by 28 units.

The overall process for mass spectrometry includes a number of steps, specifically, the ionization of the peptides, acquisition of a full spectrum (survey scan) and selection of specific precursor ions to be fragmented, fragmentation, and acquisition of MS/MS spectra (product-ion spectra). The data is processed to either quantify the different species and/or determine the peptide amino acid sequence. Since the number of ion populations generated by MS exceeds that which standard instruments can individually target for sequence analysis with a tandem mass spectrum scan, it is often necessary to control the data acquisition process and manage the limited scan speed. Data-dependent acquisition (DDA) performs a precursor scan to determine the mass-to-charge ratio (m/z) and abundance of ions eluting from the LC column at a particular time (often referred to as MS1 scan). This initial precursor scan allows for identification and screening of the most intense ion signals (precursor ions), which are then selected for subsequent fragmentation and selection in the second part of MS/MS. In MS/MS, this precursor scan is followed by isolation and fragmentation of selected peptide ions using sequence determining MS/MS scans (often referred to as MS2 scan) to generate a mass spectra.

As used herein "precursor ions" and "precursor ion signals" refer to ions and MS peak signals identified during MS1 scanning of tandem mass spectrometry.

As used herein "fragment ions" and "fragment ion signals" refer to ions generated by mass spectrometry, such as precursor ions or MS peak signals identified during MS2 scanning of tandem mass spectrometry.

Various challenges exit for interpreting mass spectrometry data. For de novo sequencing, exactly one out of $20^L$ amino acid sequences can be considered as the correct prediction (L is the peptide length, 20 is the total number of possible amino acids). One challenge to de novo sequencing from mass spectrometry data is that peptide fragmentation generates multiple types of ions including a, b, c, x, y, z, internal cleavage and immonium ions. Depending on the fragmentation methods, different types of ions may have quite different intensity values (peak heights), and yet, the ion type information remains unknown from spectrum data.

Furthermore, there are plenty of noise peaks mixing together with the real ions. Finally, the predicted amino acid sequence should have its total mass approximately equal to the given peptide mass. This points to a complicated problem of pattern recognition and global optimization on noisy and incomplete data.

Accordingly, the present inventors have developed improved systems that allow for deep learning to be applied in de novo peptide sequencing. In some embodiments, the systems provided herein allows for greater accuracy of reconstructing peptide sequences, and lower computational and processor requirements thereby reducing costs and energy consumption for de novo sequencing. Systems incorporating artificial neural networks described here also allows for greater coverage in terms of peptides that can be sequenced by de novo peptide sequencing. As well, in some embodiments, access to external databases are not needed.

Mass Spectra Data Format

Mass spectrometry data is stored, for example, as a mass spectra or a plot of the ion signal as a function of the mass-to-charge ratio (m/z), a data table listing ion signal and related mass-to-charge ratio, a data string comprising pairs of ion intensity signal and related m/z, where values can be stored in corresponding data fields and data instances. The mass spectra data sets may be stored in various data structures for retrieval, transformation, and modification. Such data structures can be, for example, one or more tables, images, graphs, strings, maps, linked lists, arrays, other data structure, or a combination of same.

In one embodiment, a mass spectra data contains coordinate data of multiple fragment ion peaks, each of which is represented as a coordinate pair of mass-to-charge ratio and intensity (m/z; intensity). In some mass spectrometry systems, the output of the mass spectrometer is a mass spectra data in the form of coordinate pair of m/z and intensity. Previously, mass spectra data was converted into intensity vectors for de novo sequencing by neural networks, as it was thought that this step was needed to allow for feature extraction. However, conversion of mass spectra data into intensity vectors results in loss of useful information, which in turn reduces the accuracy of subsequent de novo sequencing. Directly using coordinate data comprising pairs of m/z and intensity, and without conversion into a vector format, allows for a more accurate representation of the mass spectra data.

In accordance with the present disclosure, the present inventors have developed neural network based systems and methods for de no sequencing, that directly utilize coordinate data comprising pairs of m/z and intensity. Previously it was considered that conversion of mass spectra data into intensity vectors was necessary for feature extraction, which outweighed the loss of information during conversion. However, the present inventors have developed a neural network based model for de novo sequencing that still allows for feature extraction when the spectrum data is represented as coordinate data comprising pairs of m/z and intensity. In addition, the present inventors have surprisingly discovered that directly using coordinate data comprising pairs of m/z and intensity with the neural network based model increased the accuracy of de novo sequencing results, compared to using intensity vectors with previous neural network based models.

In some embodiments, the output data of a mass spectrometer is inputted into an artificial neural network configured for de no sequencing, without conversion of the data into intensity vectors. In some embodiments, the output data of a mass spectrometer comprises pairs of m/z and intensity representing fragment ion peaks. In one embodiment, a mass spectrometer outputs at least 300 pairs of m/z and intensity data and/or up to 1000 or more pairs at maximum. Some mass spectrometers are configured to output more than 1000 pairs of m/z and intensity for each sample analysis, while other can only output around 1000 pairs or less. The maximum data output of a mass spectrometer is limited by the capacity of the machinery.

In some embodiments, a subset of the output data of a mass spectrometer is used for de novo sequencing with artificial neural networks. In one embodiment, a subset of fragment peaks having the greatest intensity is selected for de novo sequencing. In one embodiment, the top 50%, 60%, 70%, 80%, 90%, or 95% of data pairs having greatest intensity values is selected for de novo sequencing. In some embodiments, the percentile cut-off is pre-determined experimentally based on the dataset or peptide sample. In one embodiment, the top 1000, 900, 800, 700, 600, 500, 400, or 300 data pairs having greatest intensity values are selected for de novo sequencing. In alternate embodiments, all the output data of a mass spectrometer is used for de novo sequencing with artificial neural networks.

Neural Network

In some embodiments, a processor and at least one memory provides a plurality of layered nodes to form an artificial neural network. The process is configured to determine the amino acid sequence of a peptide. In some embodiments, the plurality of layered nodes comprise at least one node configured to receive: 1) mass spectra data comprising a plurality of coordinate data pairs (m/z; intensity) of observed fragment ion peaks, and 2) coordinate data of theoretical fragment ion peaks.

In some embodiments, the system comprises a processor and at least one memory providing a plurality of layered nodes configured to form an artificial neural network for generating a probability measure for one or more candidates to a next amino acid in an amino acid sequence. The artificial neural network is trained on known mass spectrometry data representing theoretical fragment ions peaks of known sequences differing in length and differing by one or more amino acids. The system receives a sequence that has been predicted up to the current iteration or position in the peptide sequence and outputs a probability measure for each of the next possible element in the sequence by interpreting the fragment ion peaks of the mass spectra. In one embodiment, the system iterates the process until the entire sequence of the peptide is determined.

In some embodiment, the artificial neural network comprises a prediction neural network that identifies amino acid sequences corresponding to the observed fragment ion peaks and generates one or more output vectors representing the amino acid sequences. In some embodiments, the artificial neural network comprises a recurrent neural network (RNN), preferably a long short-term memory (LSTM) network for predicting the next amino acid by vector embedding a vector, and for outputting the probability measure for each candidate next amino acid.

In one embodiment, the neural network artificial neural network comprises a first neural network for feature extraction, combined with a LSTM second neural network for predicting the next amino acid based on sequence patterns of peptides using a language model.

As used herein, a "prefix" refers to a sequence of amino acids that have been predicted up to the current iteration. In some embodiments, a prefix includes a "start" symbol. In one preferred embodiment, a fully sequenced peptide sequence begins with the "start" symbol and ends with an "end" symbol. The prefix is indexed, for example, using the single-letter representation of amino acids or the amino acid name. In some embodiments, a prefix is indexed as:

prefix={start,P,E,P} and the mass of this prefix ("prefix mass") is indexed as:

prefix_mass=mass[N-term]+mass[P]+mass[E]+mass[P]

In some embodiments, given a prefix input the artificial neural network is configured to identify corresponding b- and y-ions in the mass spectra data. The b- and y-ions corresponding to the next amino acid to be determined in a peptide sequence is identified. For example, given a 10 amino acid long peptide and a prefix input comprising the first 3 amino acids from the amino end of the peptide that has already been determined, the system iteratively goes through each of the 20 possible amino acids to identify candidate 4th amino acid for this peptide. Using the example of Alanine as the 4th amino acid, the mass of the prefix and the mass of the the 4th amino acid Alanine is determined. Since a mass spectrum involves the fragmentation of peptides, for a 4 amino acid long fragment from the amino end of the peptide (referred to as the b-ion), there is a corresponding 6 amino acid long fragment from the C-end of the peptide (referred to as the y-ion), using this example. The artificial neural network is configured to take these b-ions and y-ions for each candidate next amino acid in the sequence and fits the b-ions and y-ions against the mass spectra data. Matches with a coordinate pair of the mass spectrum data within an error range means that these b- and y-ions are present in the fragments generated by the mass spectrometer, and in turn more likely that the candidate amino acid is the next one in the sequence.

In one embodiment, the artificial neural network is configured to identify 8 ion types (b-ion ("b"), y-ion ("y"), b(2+), y(2+), b-H2O, y-H2O, b-NH3, y-NH3) by fitting against the spectra data.

In some embodiments, given a prefix input the artificial neural network is configured to identify corresponding b-, y-, and a-ions in the mass spectra data. In addition to the b- and y-ions, the a-ion corresponding to the next amino acid to be determined in a peptide sequence is identified. Using the same example above, given a 10 amino acid long peptide and a prefix input comprising the first 3 amino acids from the amino end of the peptide that has already been determined, the system iteratively goes through each of the 20 possible amino acids to identify candidate 4th amino acid for this peptide. Using the example of Alanine as the 4th amino acid, the mass of the prefix, and the mass of the prefix plus the 4th amino acid Alanine is determined. The artificial neural network is configured to take the a-ions for each candidate next amino acid in the sequence and fits them against the mass spectra data. Matches with a coordinate pair of the mass spectrum data within an error range means that the a-ion is present in the fragments generated by the mass spectrometer, and in turn more likely that the candidate amino acid is the next one in the sequence.

In one embodiment, the artificial neural network is configured to identify 12 ion types (b-ion ("b"), y-ion ("y"), a-ion ("a"), b(2+), y(2+), a(2+), b-H2O, y-H2O, a-H2O, b-NH3, y-NH3, a-NH3) by fitting against the spectra data.

As used herein "fitting" includes comparing one coordinate data against another coordinate data to find matches. In some embodiments, the matches are identified that are within an error range.

In some embodiments, the artificial neural network outputs a probability measure for each of the next possible element in the sequence. This output is stored as, for example, data tables, vectors, data arrays, or data strings comprising pairs of candidate amino acid and the corresponding probability, where values can be stored in corresponding data fields and data instances. For example, given an input prefix comprising the first three predicted amino acids, the output for the 4$^{th}$ candidate amino acid is indexes as a probability vector: [(Alanine, 80%), (Arginine, 15%), (Asparagine, 5%)]. In some embodiments, the output is a probability distribution, summing up to a total of 100%.

Feature Extraction

As used herein, "feature extraction" refers to the transformation of input data, such as mass spectra data pairs, into a set of features, such as the corresponding amino acid or amino acid sequence.

In some embodiments, 26 possible features, represented by symbols or elements, are predicted from. In one embodiment, the 26 symbols refer to "start", "end", "padding", the 20 possible amino acids, three amino acid modifications (for example: carbamidomethylation (C), Oxidation (M), and Deamidation (NQ)) for a total of 26. The "padding" symbol refers to blanks. In one embodiment, eight ion types (b, y, b(2+), y(2+), b-H2O, y-H2O, b-NH3, and y-NH3) were considered.

In some embodiments, 26 possible features, represented by symbols or elements, are predicted from. In one embodiment, the 26 symbols refer to "start", "end", "padding", the 20 possible amino acids, three amino acid modifications (for example: carbamidomethylation (C), Oxidation (M), and Deamidation (NQ)) for a total of 26. The "padding" symbol refers to blanks. In one embodiment, twelve ion types (b, y, a, b(2+), y(2+), a(2+), b-H2O, y-H2O, a-H2O, b-NH3, y-NH3, and a-NH3) were considered.

In some embodiments, the system computes the theoretical m/z location for each token and ion type pair based on the received 1) mass spectra data comprising a plurality of coordinate data pairs (m/z; intensity) of observed fragment ion peaks, and 2) coordinate data of theoretical fragment ion peaks.

In some embodiments, the plurality of layered nodes is configured to compare an observed fragment ion peak against a theoretical fragment ion peak, and identify the m/z difference between the observed and the theoretical coordinate data. In one embodiment, the artificial network is trained on fragment ion peaks with coordinate data having small difference compared to that of a theoretical fragment ion peak. Preferably, the difference is close to zero. In one embodiment, the difference is minimized to identify a matching theoretical fragment ion peak, by constraining the difference based on equation 2:

$$\sigma(D)=\exp\{-|D|*c\} \quad (2)$$

wherein:
σ(D) is an activation function,
D is a difference tensor between the observed fragment ion peak and the theoretical fragment ion peak, and
c is a constant.

The present inventors have experimentally derived the value for constant c. In some embodiments, a value of between 50 to 150 was selected for c, preferably between 70 to 120. In one embodiment, a value of 100 was selected for c.

First Prediction Neural Network

In some embodiments, the first prediction neural network is configured for order invariant data. As used herein, "order invariant data" refers to data where the order of the data is not important. For example, mass spectra data is an order invariant data since the order of the coordinate data pairs do not matter. In one embodiment, the first prediction neural network is trained with T Net™.

In some embodiments, the first prediction neural network comprises one or more convolutional layers, and one or more fully connected layers. In one embodiment, the first prediction neural network comprises three 1D convolutional layers with kernel size 1. In one embodiment, the first prediction neural network comprises three fully connected layers. In one embodiment, the first prediction neural network comprises a global max pooling layer between the convolutional layers and the fully connected layers.

In some embodiments, the first prediction neural network is trained on one or more mass spectra of one or more known peptides. In other embodiments, the first prediction neural network is trained on one or more mass spectra with ion peaks corresponding to known peptide fragments. These known peptide fragments have varying lengths and sequences. In some embodiments, these known peptide fragments vary by one amino acid residue in length. In one embodiments, for each set of known peptide fragments of the same length, they each vary by one amino acid at a particular location. In yet other embodiments, these known peptide fragments are pairs of b-ions and y-ions. In other embodiments, these known peptide fragments are a-, y-, and a-ions.

In some embodiments, the final output of the first prediction neural network is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

RNN and LSTM

Long Short Term Memory (LSTM) networks, is a type of Recurrent Neural Network (RNN). In one embodiment, a LSTM is configured to predict the next element in a series or string based on the previous elements. For example, one could predict the next word in a sentence given the previous words. In the context of de novo peptide sequencing, a LSTM is configured to predicted the next amino acid (a symbol), given the previous ones (i.e. a prefix). As used herein, the expression "language model" refers to a prediction model based on training for patterns in a string and identifying the next element in a series or string based on the previous elements. Similarly, amino acids do not just appear in a random order in protein sequences. Instead, proteins often have particular patterns in their sequences, and a LSTM is configured to predict the next amino acid based on these patterns and the previous determined amino acids in a sequence.

In some embodiments, the artificial neural network has a further LSTM module following the first prediction neural network. The LSTM is initialized with information about the original mass spectrum or mass spectra data to output predictions about the next amino acid in a sequence. In some embodiments, an embedding matrix is used to initialize the LSTM.

In one embodiment, the embedding matrix for initializing the LSTM is a sinusoidal m/z positional embedding. For example, the sinusoidal m/z positional embedding is based on the positional embedding proposed by Vaswani et al. (2017), the entire content of which is incorporated herein by reference. A sinusoidal positional embedding is advantageous for the model described herein, since in mass spectrums the m/z differences between observed peaks contain useful information. For example, where two observed fragment ion peaks correspond to amino acid sequences that differ by one amino acid length (i.e. a first observed peak corresponds to a sequence of 3 amino acid long and a second observed peak corresponds to a sequence of 4 amino acid long), the m/z difference between the two observed fragment ion peak corresponds to the mass of the 4th amino acid. Accordingly, the m/z differences between observed peaks indicate which amino acids possibly exit in a peptide sequence. By using the sinusoidal positional embedding, information is extracted from the m/z difference.

In one embodiment, the original mass spectra data is represented as spectrum representation S:

$$S = \sum_{i=1}^{N} I_i E_i \tag{4}$$

wherein:
S is the represented spectrum data,
N is the number of data pairs representing m/z and intensity values of fragment ion peaks,
I is intensity, and
E is positional embedding for m/z.

In some embodiments, the positional embedding matrix is set as a constant of two dimensional matrix of position-specific values. In other embodiments, the positional embedding matrix is set as "learnable parameters", i.e. trained together with other model parameters.

In some embodiments, the LSTM is initialized with a spectrum CNN (see US Patent Publication No. 20190018019, the entire contents of which is incorporated herein by reference). In some embodiments, the spectrum CNN is configured to encode the intensity vectors from mass spectra into "feature vectors", before the features vectors are inputted into a LSTM network. In some embodiments, the spectrum CNN comprises one or more convolutional layers, preferably two layers, and one or more fully-connected layer. In some embodiments, the spectrum CNN is configured to detect the fragment ion peaks of a mass spectrum by image processing. The spectrum CNN is configured to first slice each input intensity vector into pieces based on the amino acid masses. For example, the mass of Alanine, or "A", is 71.0 Da and if the intensity vector has mass ranges of 0.1 Da, the intensity vector is sliced by every index of 710 till the end, converting the intensity vector into a feature vector. The sliced vectors are inputted through the spectrum CNN, and outputted as a vector of a size corresponding to the number of neuron units of the last fully-connected layer. The output from spectrum CNN is inputted into a LSTM.

In preferred embodiments, the LSTM is initialized with a positional embedding matrix. As compared to LSTM initialized using a spectrum CNN, replacing the spectrum CNN with a positional embedding matrix provides advantages such as reduced number of parameters, reduced computational and processing requirements, and reduced processing costs and energy requirements.

In some embodiments, the LSTM comprises at least one layer. In preferred embodiments, the LSTM comprises 2 or 3 layers. In other embodiments, each layer comprises 128-2000 neuron units, preferably, 512 neuron units. The LSTM is configured to embed the inputted vectors (such as the vector of size 512) to represent each of the, for example, 26 symbols into a 2-dimensional array. The system iteratively inputs the vector of size 512 through the LSTM, and outputs a predicted candidate next amino acid in the sequence.

In other embodiments, the LSTM is configured to embed the inputted vectors according to the systems and procedures described in U.S. patent application Ser. No. 15/599,431, publication no. US20170336419A1, titled METHODS AND SYSTEMS FOR ASSEMBLY OF PROTEIN SEQUENCES, the entire content of which is incorporated herein by reference.

In some embodiments, the LSTM further comprises a last fully-connected layer of 26 neuron units, or as many neuron units as there are possible elements at a given position in a sequence, to perform a linear transformation of the vector of 512 output into signals of 26 symbols to predict. In one embodiment, the output from the last fully-connected layer is a probability measure for each of the possible 26 symbols.

In some embodiments, the final output of the artificial neural network comprising a first prediction neural network and a second LSTM neural network is a vector of 26 signals, or logits vector (unscaled log probabilities), corresponding to the probability of each of the 26 possible symbols being the next element in the sequence. To identify the next amino acid in a peptide sequence, the amino acid or symbol with the highest probability is chosen.

Other Embodiments

In one embodiment, while selecting the next amino acid, the system is configured to calculate the suffix mass and employs knapsack dynamic programming to filter out those amino acids whose masses do not fit the suffix mass. As used herein, "suffix mass" refers to the sum total mass of the amino acids remaining to be predicted. The prefix mass and the suffix mass must add up to equal the total mass of the peptide that is being sequenced. In embodiments where knapsack is applied to filter out amino acids whose masses do not fit the suffix mass; the recall and/or accuracy of the system were increased.

In some embodiments, the system performs bi-directional sequencing and uses two separate sets of parameters, forward (for example, sequencing from the amino end of the peptide) and backward (for example, sequencing from the carboxylic end of the peptide).

In some embodiments, the system is configured to predict the next amino acids using a beam search to optimize the prediction. As used herein "beam search" refers to a heuristic search where instead of predicting the next element in a sequence one at a time at each iteration based on probability, the next n-elements are predicted based on the overall probability of the n-elements. For example, where n=5, the system predicts the next 5 amino acids at a time in the sequence at each iteration based on the an overall probably of the next 5 candidate amino acids sequences which is derived from the product of each individual amino acid probabilities.

In some embodiments, there is provided a computer implemented system for de novo sequencing of peptides from mass spectrometry data using neural networks, the system including one or more processors and non-transitory computer readable media, the computer implemented system comprising: a mass spectrometer configured to generate a mass spectrometry data of a peptide (or, in some embodiments, a portion of a peptide or a biological sequence or portion thereof); a processor configured to: generate an input prefix representing a determined amino acid sequence of the peptide. In some embodiments, the determined amino acid sequence of the peptide can include a sequence of one or more amino acids. In some embodiments, the determined amino acid sequence of the peptide can include a "start" symbol and one or more or zero amino acids that have been predicted up to the current iteration. The processor, in these embodiments, is further configured to iteratively update the determined amino acid sequence with a next amino acid. In these embodiments, the computer implemented system comprises a neural network configured to iteratively generate a probability measure for one or more candidate fragment ions (e.g., a candidate fragment ion can be a fragment ion having a particular amino acid at a particular location in the sequence as compared to a separate candidate fragment ion that has a different particular amino acid at that same particular location in the sequence). In some embodiments, there may be a candidate fragment ion each corresponding to each of 20 amino acid residues, their modifications, and special symbols. The iterative generation of a probability measure may be based on one or more fragment ion peaks of the mass spectrometry data and the corresponding masses of the fragment ion peaks, to determine the next amino acid, wherein the neural network is trained on a known mass spectrometry data. In some embodiments, the neural network comprises: at least one convolutional layer configured to apply one or more filters to an image data representing the mass spectrometry data to detect fragment ion peaks; and at least one fully-connected layer configured to determine the presence of a fragment ion peak corresponding to the next amino acid and output the probability measure for each candidate fragment ion.

Workflow

Figure 4:
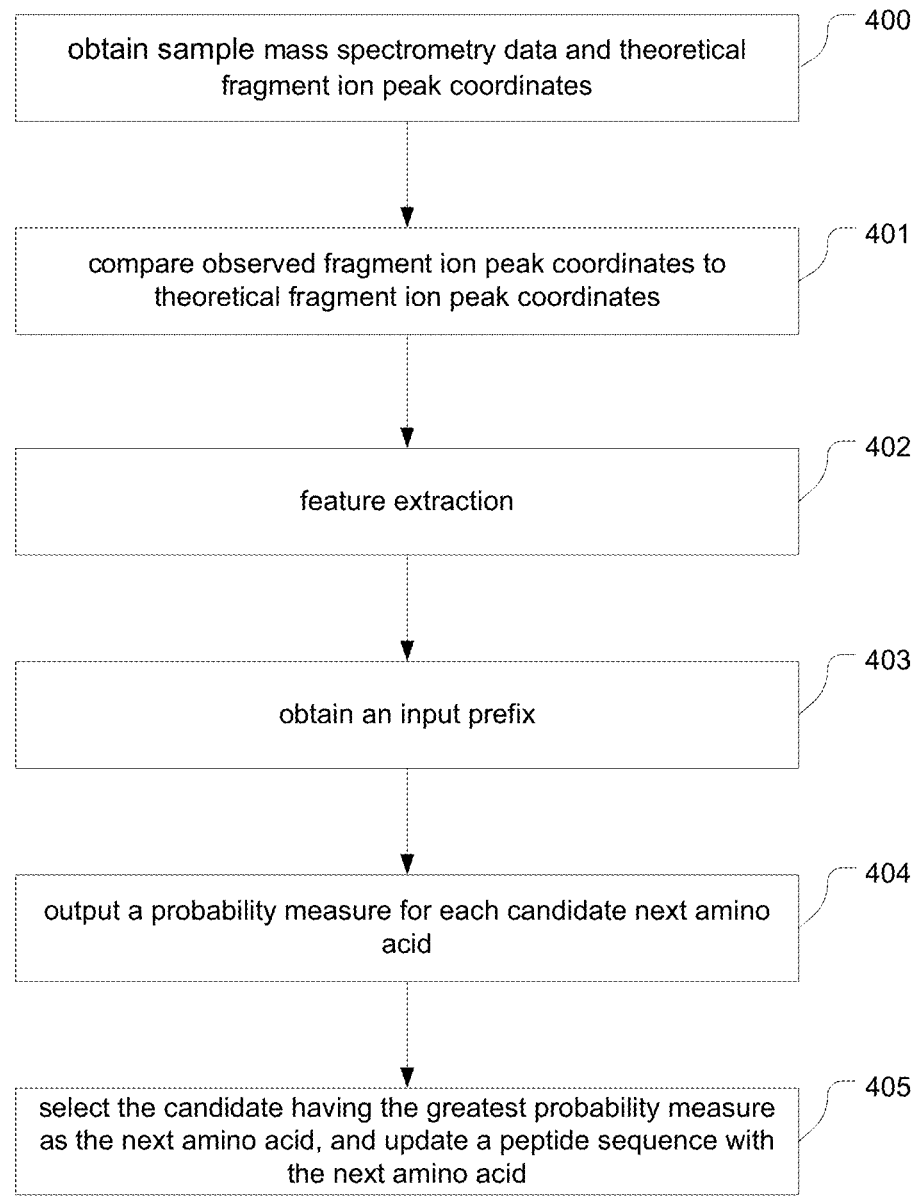
FIG. 4 shows a flow chart of an example de novo sequencing procedure using neural networks.

FIG. 4 is a flow chart of an example procedure for de novo sequencing of a peptide using artificial neural networks and mass spectrometry data. A sample mass spectrometry data comprising observed fragment ion peak coordinates, and theoretical fragment ion peak coordinates are obtained 400 and received by the artificial neural network. The coordinates of the observed fragment ion peaks are compared against the theoretical fragment ion peaks 401, to extract features from the sample mass spectrometry data 402.

The extracted features are outputted at feature vectors from a first neural network. The feature vectors are concatenated to a second neural network (such as an LSTM). To generate a sequence for the peptide, an input prefix is obtained 403 representing a portion of the peptide sequence that have been determined up to that point. A probability measure is then determined for each candidate of the next amino acid in the peptide sequence 404. The candidate having the greatest probability measure based on the output of the artificial neural network and the sample mass spectrometry data is selected as the next amino acid, and the determined peptide sequence is updated with this next amino acid 405. This process is repeated until the full peptide sequence is determined.

Sequence Output

In some embodiments, the processors and/or the system is configured to generate signals for outputting at least a portion of the determined sequence. In some embodiments, the output can represent at least a partially determined sequence. In some embodiments, the output can represent one or more partially determined sequences. In some instances, the one or more partial determined sequences can be combined into a fully determined sequence. In some embodiments, the output can include a fully determined sequence or a portion of the fully determined sequence.

In some embodiments, generating signals for outputting at least a portion of a determined sequence can include generating signals for display the output on a visual display or screen, generating signals for printing or generating a physical representation of the output, generating signals for providing an audio representation of the output, sending a message or communication including the output, storing the output in a data storage device, generating signals for any other output and/or any combination thereof.

In some instances, the determined sequence outputted by the systems provided herein is used for novel protein discovery, for example, for antibody characterization. In some embodiments, the determined sequences outputted by the systems provided herein is used for generating antibodies for diagnostic kits or diagnostic imaging. In some embodiments, the determined sequences outputted by the systems provided herein is used for generating antibodies for new disease therapies. In some embodiments, the determined sequences outputted by the systems provided herein is used for generating antibodies for prenatal therapy. In some embodiments, the determined sequences outputted by the systems provided herein is used for vaccine development. In some embodiments, the determined sequences outputted by the systems provided herein is used for developing immunoassays.

Computing Device

Figure 5:
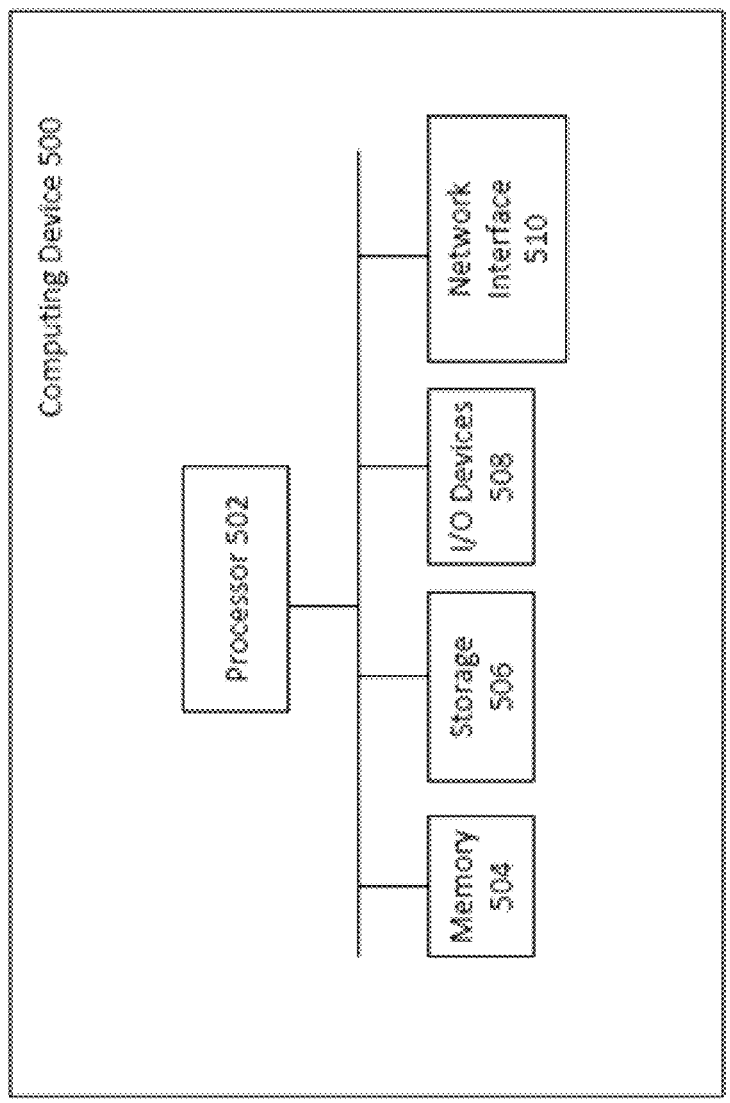
FIG. 5 shows a block diagram of an example computing system configured to perform one or more of the aspects described herein.

FIG. 5 is a block diagram of an example computing device 500 configured to perform one or more of the aspects described herein. Computing device 500 may include one or more processors 502, memory 504, storage 506, I/O devices 508, and network interface 510, and combinations thereof. Computing device 500 may be a client device, a server, a supercomputer, or the like.

Processor 502 may be any suitable type of processor, such as a processor implementing an ARM or x86 instruction set. In some embodiments, processor 502 is a graphics processing unit (GPU). Memory 504 is any suitable type of random access memory accessible by processor 502. Storage 506 may be, for example, one or more modules of memory, hard drives, or other persistent computer storage devices.

I/O devices 508 include, for example, user interface devices such as a screen including capacity or other touch-sensitive screens capable of displaying rendered images as output and receiving input in the form of touches. In some embodiments, I/O devices 508 additionally or alternatively include one or more of speakers, microphones, sensors such as accelerometers and global positioning system (GPS) receivers, keypads, or the like. In some embodiments, I/O devices 508 include ports for connecting computing device 500 to other computing devices. In an example embodiment, I/O devices 508 include a universal serial bus (USB) controller for connection to peripherals or to host computing devices.

Network interface 510 is capable of connecting computing device 500 to one or more communication networks. In some embodiments, network interface 510 includes one or more or wired interfaces (e.g. wired ethernet) and wireless radios, such as WiFi, Bluetooth, or cellular (e.g. GPRS, GSM, EDGE, CDMA, LTE, or the like). Network interface 510 can also be used to establish virtual network interfaces, such as a Virtual Private Network (VPN).

Computing device 500 operates under control of software programs. Computer-readable instructions are stored in storage 506, and executed by processor 502 in memory 504. Software executing on computing device 500 may include, for example, an operating system.

The systems and methods described herein may be implemented using computing device 500, or a plurality of computing devices 500. Such a plurality may be configured as a network. In some embodiments, processing tasks may be distributed among more than one computing device 500.

EXAMPLES

DeepNovoV2

Figure 2:
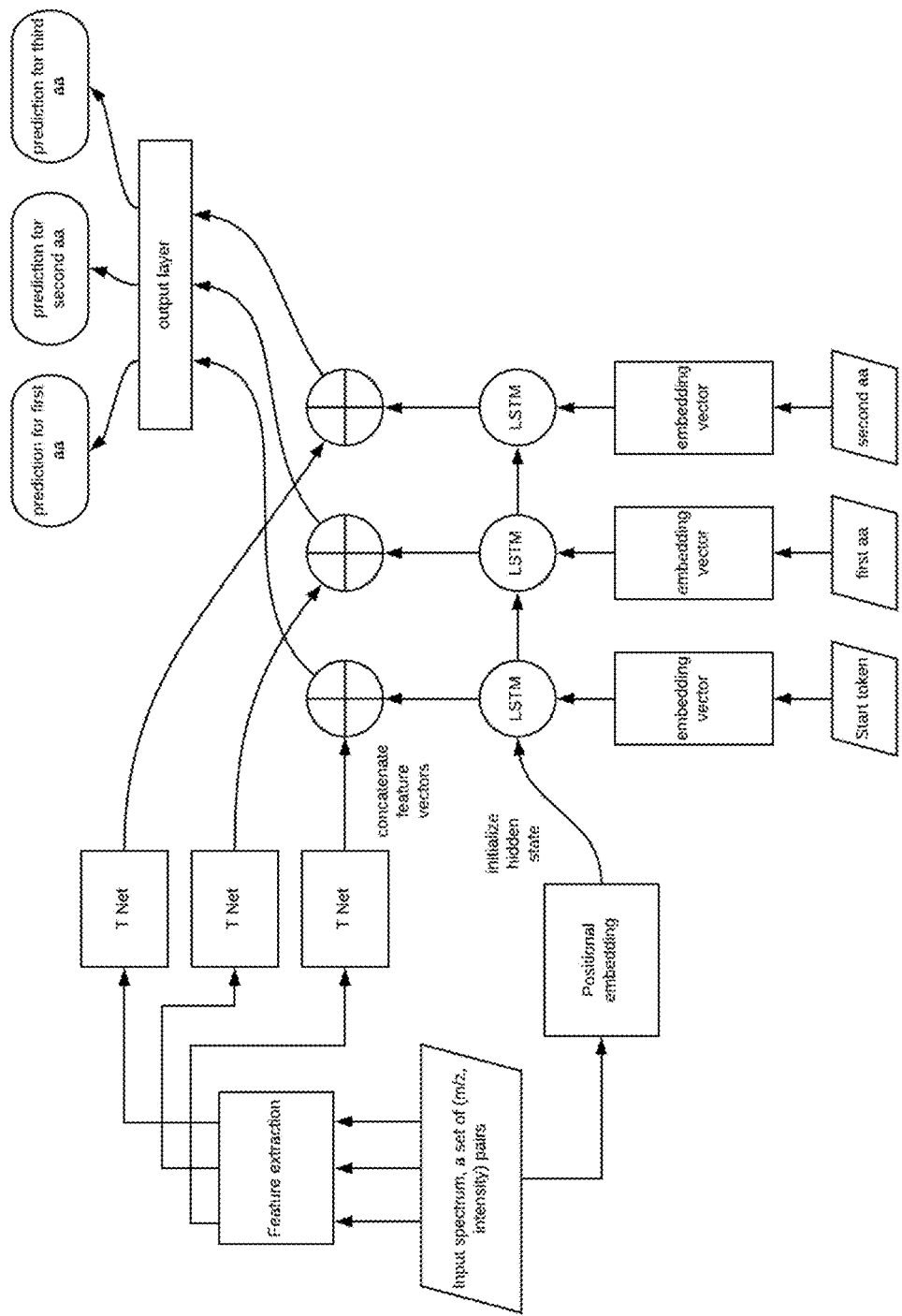
FIG. 2 shows a flow chart of the architecture of the DeepNovoV2 artificial neural network.
Figure 3:
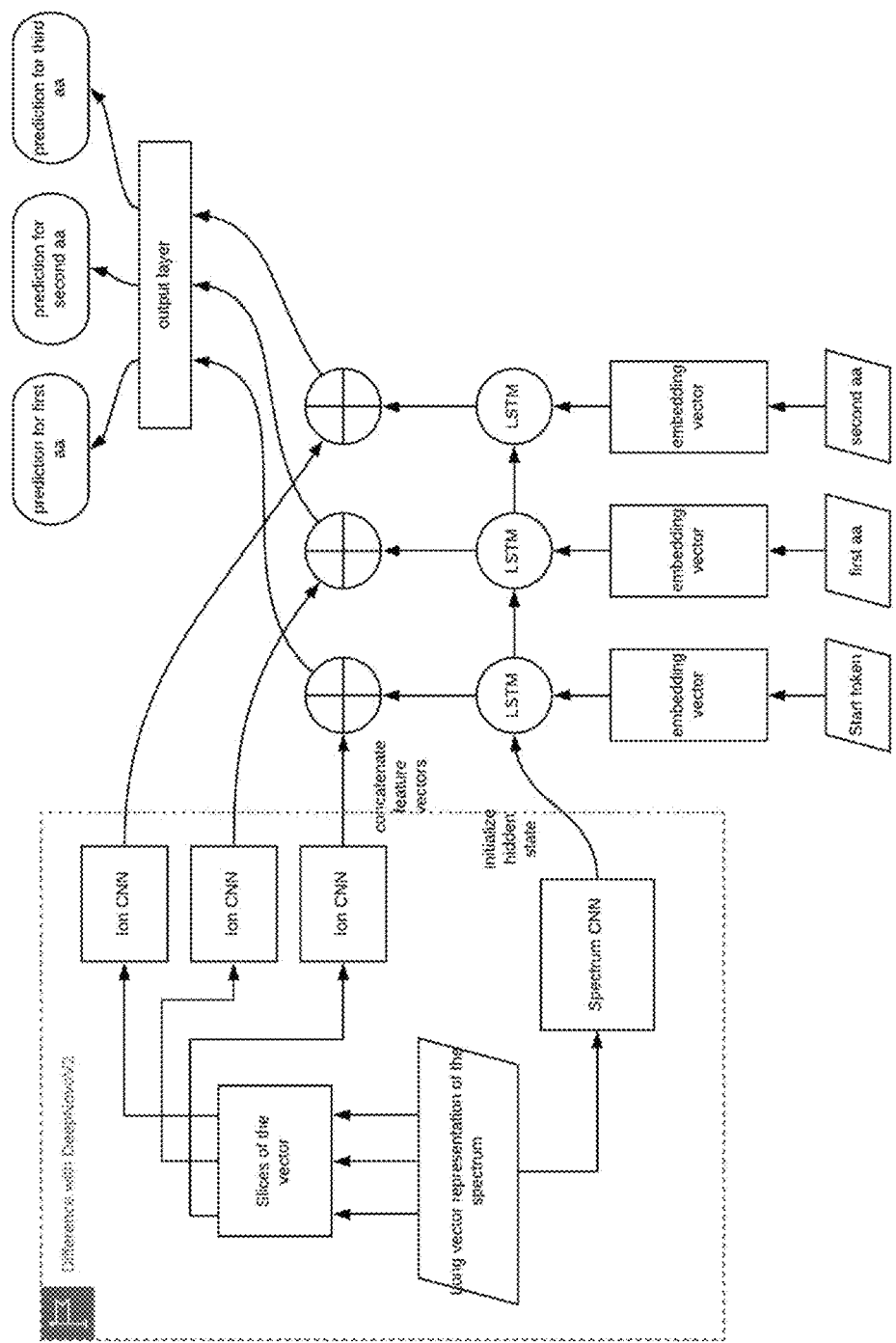
FIG. 3 shows a flow chart of the architecture of the DeepNovo artificial neural network. The dashed line portion indicates the portion of the architecture of DeepNovo that was modified to generate the DeepNovoV2 artificial neural network shown in FIG. 2.

DeepNovoV2 is an improved model for de novo peptide sequencing, the architecture of which is shown in FIG. 2. As shown in FIG. 3, the previous DeepNovo model was modified to develop DeepNovoV2. Experiment results on several DDA MS datasets showed that DeepNovoV2 provided improvements over DeepNovo by a significant margin of at least 15% increase in accuracy on peptide level.

Methods

Spectrum Representation.

Previously in DeepNovo, spectrums were represented as intensity vectors, where each index of the vector represents a small m/z bin and the value represents the sum of intensities of all peaks fall into that bin. This representation of spectrum faces challenges in terms of accuracy and speed/memory trade off. For example, by default DeepNovo used a spectrum resolution of 10, which meant that every peak within a 0.1 m/z bin was merged together and represented as an element of the intensity vector. However, useful information on the exact location of each peak was lost during the merging. On the other hand, building a more accurate model by increasing the resolution results in significantly longer intensity vectors and the model would require more memory and time for training, resulting in greater costs and greater processing power requirements. In DeepNovoV2, to solve the accuracy-speed/memory trade off problem, MS data was directly represented as a set of (m/z, intensity) pairs. For each spectrum the top N most intense peaks were selected, and the spectrum was represented as: $\{(m/z_i, I_i)\}_{i=1}^{N}$. Further, we denote $M_{observed} = (m/z_1, \ldots, m/z_N)$ as the observed m/z vector and $I = (I_1, \ldots, I_N)$.

Feature Extraction.

The number of tokens was denoted as $n_{vocab}$ and number of ion types as $n_{ion}$. For fair comparison with DeepNovo, the following were selected: $n_{vocab} = 26$ (20 amino acid residues, 3 variable modifications and three special tokens: "start", "end" and "pad") and the same eight ion types (b, y, b(2+), y(2+), b-H2O, y-H2O, b-NH3, and y-NH3) as in the original implementation of DeepNovo[8] was used. At each step, the theoretical m/z location for each token and ion type pair was computed. The result was a matrix of shape $(n_{vocab}, n_{ion})$ and denoted as $M_{theoretical}$. Next the dimension of $M_{observed}$ was expanded into a 3-dimensional tensor of shape (N; 1; 1), and then $M_{observed}$ was repeated on the second dimension for $n_{vocab}$ times and on the third dimension for $n_{ion}$ times. The result was denoted as $M'_{observed}$, a tensor of shape (N, $n_{vocab}$, $n_{ion}$). Similarly $M_{theoretical}$ was expanded to the shape of (1, $n_{vocab}$, $n_{ion}$), repeated on the first dimension for N times and the result was denoted the result as $M'_{theoretical}$. Then the m/z difference tensor was computed (denoted as D, see equation 1) in which each element represents the difference between the m/z value for an observed peak and the theoretical m/z for a token and ion type pair.

$$D = M'_{observed} - M'_{theoretical} \quad (1)$$

In some cases, Equation 1 could be computed efficiently using the "broadcast" behaviour in popular frameworks, for example, Tensorflow™[14] and PyTorch™[15].

$$\sigma(D) = \exp\{-|D|*c\} \quad (2)$$

An activation function $\sigma(D)$ was designed, as shown in Equation 2. Here the exponential and absolute operations are all element wise operations. The intuition for $\sigma$ was that an observed peak could only be considered as matching a theoretical m/z location if the absolute m/z difference is small. For example, if c=100, then an observed peak that was 0.02 Da away from a theoretical location would generate a signal of $e^{-2} \approx 0.135$, which was only one seventh of the signal of a perfect match. In the experiments, c was set to be a trainable parameter and updated through backpropagation. It showed similar performance with setting c=100, thus for the simplicity and efficiency of the model, c was fixed at 100.

$$F = \sigma(D)' \oplus I' \quad (3)$$

The feature matrix F for prediction was the concatenation of $\sigma(D)$ and intensity (I), as shown in Equation 3. Here $\sigma(D)'$ is a N by $n_{vocab} \times n_{ion}$ matrix reshaped from $\sigma(D)$, I' is a N by 1 matrix reshaped from I and $\oplus$ represents concatenation along the second dimension.

T Net

The spectrum was represented as set of (m/z; intensity) pairs, which meant that the order of peaks should be irrelevant. Therefore, the prediction neural network should have order invariant property with respect to the first dimension of F. T Net™ (the building block of Point Net™[16]) was to process F, given the order invariant data. T Net was composed of three 1d convolutional layers with kernel size 1, followed by a global max pooling layer and 3 fully connected layers. An Long short-term memory (LSTM) aside from the T net was added to make use of the language model information of peptides. The structure for T Net is shown in FIG. 1 and the full model structure of DeepNovoV2 is shown in FIG. 2. Focal loss[13] instead of cross entropy loss was used when training the model.

The input data to the prediction neural network was a prefix, i.e., a sequence including the "start" symbol and the amino acids that have been predicted up to the current iteration. The output was a probability distribution over 20 amino acid residues, their modifications, and three special symbols "start", "end", and "padding". For example, three modifications were considered: fixed modification carbamidomethylation (C), and variable modifications Oxidation (M) and Deamidation (NQ), hence, a total of 26 symbols was used for prediction. For example, where the fourth amino acid was considered, the prefix consisted of four symbols "start", "P", "E", "P". Symbol "T" was predicted as the next amino acid (4th amino acid in this example) by sampling or by selecting the highest probability from the model output probability distribution.

Given the input prefix (prefix={start, P, E, P}), DeepNovoV2 first computed the prefix mass (prefix_mass=mass[N-term]+mass[P]+mass[E]+mass[P]), i.e., the sum of masses of N-terminal and amino acids in the prefix. Next, DeepNovoV2 tried to add each of 26 symbols to the current prefix and updated its mass accordingly. For each candidate, the corresponding masses of b-ions and y-ions were calculated and identified in the spectrum (m/z, intensity) pair. In the current implementation, 12 ion types were used: b, y, a, b(2+), y(2+), a(2+), b-$H_2O$, y-$H_2O$, a-$H_2O$ b-$NH_3$, y-$NH_3$ and a-$NH_3$.

Initial State for LSTM

A LSTM module was included to capture the "language model" for peptides. To make good predictions about the next amino acid, it was important for the LSTM to be initialized with information about the original spectrum. In previous DeepNovo a spectrum CNN was used to extract features from intensity vectors and then used the extracted features to initialize the LSTM. In DeepNovoV2, the spectrum CNN structure was replaced with a simple embedding matrix. Specifically, a sinusoidal m/z positional embedding was created, based on Vaswani et al[17]:

$$PE_{(loc,2i)} = \sin(loc/10000^{\frac{2i}{d_{lstm}}})$$

$$PE_{(loc,2i+1)} = \cos(loc/10000^{\frac{2i}{d_{lstm}}})$$

Here loc represents the m/z location after discretization, and $d_{lstm}$ represents the dimension of the LSTM module. This sinusoidal embedding has a desired property that for any distance k, $PE_{loc+k}$ could be represented as a linear function of $PE_{loc}$[17]. This property was important because in mass spectrums the m/z differences between observed peaks contain useful information that indicates which amino acids possibly exist. By using the sinusoidal positional embeddings, the model could learn to extract information from the m/z difference between peaks.

For each spectrum $\{(m/z_i, I_i)\}_{i=1}^{N}$, the positional embedding for $m/z_i$ was denoted as $E_i$. The spectrum representation S was computed by:

$$S = \sum_{i=1}^{N} I_i E_i \quad (4)$$

Then the initial hidden states ho and co was both initialized to S. By replacing spectrum CNN with a fixed positional embedding matrix, the number of parameters and computation needed in the model was reduced. Experimental result showed that initializing with S gave similar results comparing to initializing with the result of spectrum CNN.

LSTM

Long Short Term Memory (LSTM) networks, one type of Recurrent Neural Networks (RNNs), has an application of which is for the handling of sequential data in Natural Language Processing and Speech Recognition. RNNs are called "recurrent" because they repeat the same computations on every element of a sequence and the next iteration depends on the networks' "memory" of previous steps. For example, one could predict the next word in a sentence given the previous words. In de novo peptide sequencing, DeepNovoV2 predicted the next amino acid (a symbol), given the previous ones (i.e. the prefix), based on the fact that amino acids do not just appear in a random order in protein sequences. Instead, proteins often have particular patterns in their sequences.

The LSTM model of DeepNovoV2 represented each amino acid class by an embedding vector, i.e., a collection of parameters that characterize the class (similar to word2vec). Given a prefix, the model looked for the corresponding embedding vectors and sequentially put them through the LSTM network.

First, DeepNovoV2 used embedding vectors of size 512 to represent each of 26 symbols, in a manner similarly to word2vec approach that used embedding vectors to represent words in a vocabulary. The embedding vectors formed a 2-dimensional array Embedding$^{26 \times 512}$. Thus, the input to the LSTM model at each iteration was a vector of size 512. Second, the output of the fixed positional embedding matrix was used to initialize the LSTM model, i.e. being fed as the 0-input. Lastly, the LSTM architecture consisted of 1 layer of 512 neuron units and dropout layers with probability 0.5 for input and output. DeepNovoV2 also added a fully-connected layer of 26 neuron units to perform a linear transformation of the LSTM 512 output units into signals of 26 symbols to predict.

LSTM networks often iterate from the beginning to the end of a sequence. However, to achieve a general model for diverse species, it was better to apply LSTM on short k-mers.

Training

To train DeepNovoV2, a dataset is randomly partitioned into three sets: training, validation, and testing. As described herein, due to the one-to-many relationship between peptide and spectra, it is important to make sure that the three sets do not share peptides to avoid over-fitting. The training dataset is processed in mini-batches. At each training step, a mini-batch is randomly selected from the training dataset and fed to the model. The model is provided with a real prefix and is asked to predict the next amino acid.

A loss function was used, called focal loss. Lin et al. (2017) proposed focal loss to solve the class imbalance issue in object detection, which dynamically scaled cross entropy loss. For a binary classification problem, y∈{0,1} was denoted as the ground truth class for a data point, and p as the model's predicted probability for class 1. Then the focal loss was defined by the following Equation 5:

$$\text{Focal Loss} = -(1-p_t)^\gamma \log(P_t) \quad (5)$$

where $p_t = p$ if y is class 1 and $p_t = 1-p$ if y is class 0, $\gamma$ is a hyperparameter greater than 1.

From the formula above, it could be seen that, compared to cross entropy loss, focal loss scales down the loss by a ratio of $(1-p_t)^\gamma$. This meant that focal loss down weights the contribution of easy examples (where $1-p_t$ is small), therefore the model would focus more on hard examples.

For DeepNovoV2, focal loss was selected for training. During training, the activation function of last layer was changed from softmax function to sigmoid function thus the model would give a probability between 0 and 1 for each of the 26 classes (note that here the sum of these 26 probabilities might not equal 1). Then for each class the binary classification focal loss could be computed for each class using the Equation 5 and the average of those 26 losses was used as the final loss. At inference time the activation function was switched back to softmax as this was found to lead to better performance.

MS/MS data has a special property: the same peptide could appear multiple times in a dataset with different spectra. Such spectra may have different fragment ions, and even if they share some major ions, the intensities of those ions also vary from spectrum to spectrum. However, the DeepNovoV2 was able to learn some common features of different spectra that come from the same peptide, and those features were not generalized well to other peptides. This problem would lead to over-fitting if a dataset was randomly partitioned into training, validation, and testing sets. To avoid or minimize over-fitting, the training, validation, and testing sets were partitioned such that they do not share common peptides. Preferably, more data from a wide variety of sources would be collected rather than increasing data from the same source.

Training Parameters.

DeepNovoV2 was trained with Adam™ algorithm[18] with an initial learning rate of $10^{-3}$. After every 300 training steps, the loss on validation set was computed. If the validation loss had not achieved a new low in the recent ten evaluations, then the learning rate was dropped by half.

Results and Analysis

The present model was tested on several different DDA dataset. The train-valid-test was split such that the training, validation and testing sets did not share any common peptides. On each dataset, both DeepNovo and DeepNovoV2was trained for for 20 epochs. The weights with the smallest validation error was then selected to do beam search and the metrics compared are amino acid tag mass accuracy and peptide accuracy. The result on ABRF DDA data is shown in Table 1. DeepNovoV2 was also tested with the cross species data (see Tran et al., 2017[8]), the result is shown in Table 2 and 3.

TABLE 1

Accuracy on ABRF DDA data (DeepNovo ("DN"); DeepNovoV2 ("DNV2"))

| | DN without LSTM | DN with LSTM | DNV2 without LSTM | DNV2 with LSTM |
|---|---|---|---|---|
| amino acid recall | 66.59% | 68.89% | 72.51% | 72.51% |
| peptide recall | 29.39% | 32.92% | 37.25% | 39.11% |

TABLE 2

Cross species training on 8 different species, test on Human.

| | DeepNovo | DeepNovoV2 |
|---|---|---|
| amino acid recall | 51.6% | 61.43% |
| amino acid precision | 51.0% | 60.23% |
| peptide recall | 29.3% | 35.13% |

TABLE 3

Cross species training on 8 different species, test on Mouse.

| | DeepNovo | DeepNovoV2 |
|---|---|---|
| amino acid recall | 52.7% | 63.26% |
| amino acid precision | 52.3% | 62.62% |
| peptide recall | 28.6% | 35.45% |

All publications, patents, and patent applications referred to herein are incorporated herein by reference in their entirety.

While particular embodiments of the present invention have been illustrated and described, it would be obvious to those skilled in the art that various other changes and modifications can be made. The claims should therefore not be limited by the above described embodiment, systems, methods, and examples, but should be given the broadest interpretation within the scope and spirit of the invention as claimed.

REFERENCES

[1] Ngoc Hieu Tran, M Ziaur Rahman, Lin He, Lei Xin, Baozhen Shan, and Ming Li. Complete de novo assembly of monoclonal antibody sequences. Scientific reports, 6:31730, 2016.

[2] Ngoc Hieu Tran, Rui Qiao, Lei Xin, Xin Chen, Chuyi Liu, Xianglilan Zhang, Baozhen Shan, Ali Ghodsi, and Ming Li. Deep learning enables de novo peptide sequencing from data-independent-acquisition mass spectrometry. Nature methods, 16(1):63-66, 2019.

[3] Vlado Dan˘cik, Theresa A Addona, Karl R Clauser, James E Vath, and Pavel A Pevzner. De novo peptide sequencing via tandem mass spectrometry. Journal of computational biology, 6(3-4):327-342, 1999.

[4] J Alex Taylor and Richard S Johnson. Implementation and uses of automated de novo peptide sequencing by tandem mass spectrometry. Analytical chemistry, 73(11): 2594-2604, 2001.

[5] Bin Ma, Kaizhong Zhang, Christopher Hendrie, Chengzhi Liang, Ming Li, Amanda Doherty-Kirby, and Gilles Lajoie. Peaks: powerful software for peptide de novo sequencing by tandem mass spectrometry. Rapid communications in mass spectrometry, 17(20):2337-2342, 2003.

[6] Ari Frank and Pavel Pevzner. Pepnovo: de novo peptide sequencing via probabilistic network modeling. Analytical chemistry, 77(4):964-973, 2005.

[7] Bernd Fischer, Volker Roth, Franz Roos, Jonas Grossmann, Sacha Baginsky, Peter Widmayer, Wilhelm Gruissem, and Joachim M Buhmann. Novohmm: a hidden markov model for de novo peptide sequencing. Analytical chemistry, 77(22):7265-7273, 2005.

[8] Ngoc Hieu Tran, Xianglilan Zhang, Lei Xin, Baozhen Shan, and Ming Li. De novo peptide sequencing by deep learning. Proceedings of the National Academy of Sciences, 114(31):8247-8252, 2017.

[9] Kelvin Xu, Jimmy Ba, Ryan Kiros, Kyunghyun Cho, Aaron Courville, Ruslan Salakhudinov, Rich Zemel, and Yoshua Bengio. Show, attend and tell: Neural image caption generation with visual attention. In International conference on machine learning, pages 2048-2057, 2015.

[10] Karen Simonyan and Andrew Zisserman. Very deep convolutional networks for large-scale image recognition. arXiv preprint arXiv:1409.1556, 2014.

[11] Joseph Redmon, Santosh Diwala, Ross Girshick, and Ali Farhadi. You only look once: Unified, real-time object detection. In Proceedings of the IEEE conference on computer vision and pattern recognition, pages 779-788, 2016.

[12] Yoon Kim. Convolutional neural networks for sentence classification. arXiv preprint arXiv:1408.5882, 2014.

[13] Tsung-Yi Lin, Priya Goyal, Ross Girshick, Kaiming He, and Piotr Dollar. Focal loss for dense object detection. In Proceedings of the IEEE international conference on computer vision, pages 2980-2988, 2017.

[14] Martin Abadi, Paul Barham, Jianmin Chen, Zhifeng Chen, Andy Davis, Jeffrey Dean, Matthieu Devin, Sanjay Ghemawat, Geoffrey Irving, Michael Isard, Manjunath Kudlur, Josh Levenberg, Rajat Monga, Sherry Moore, Derek G. Murray, Benoit Steiner, Paul Tucker, Vijay Vasudevan, Pete Warden, Martin Wicke, Yuan Yu, and Xiaoqiang Zheng. Tensorflow: A system for large-scale machine learning. In 12th USENIX Symposium on Operating Systems Design and Implementation (OSDI 16), pages 265-283, 2016.

[15] Adam Paszke, Sam Gross, Soumith Chintala, Gregory Chanan, Edward Yang, Zachary DeVito, Zeming Lin, Alban Desmaison, Luca Antiga, and Adam Lerer. Automatic differentiation in pytorch. In NIPS-W, 2017.

[16] Charles R Qi, Hao Su, Kaichun Mo, and Leonidas J Guibas. Pointnet: Deep learning on point sets for 3d classification and segmentation. In Proceedings of the IEEE Conference on Computer Vision and Pattern Recognition, pages 652-660, 2017.

[17] Ashish Vaswani, Noam Shazeer, Niki Parmar, Jakob Uszkoreit, Llion Jones, Aidan N Gomez, Łukasz Kaiser, and Illia Polosukhin. Attention is all you need. In Advances in Neural Information Processing Systems, pages 5998-6008, 2017.

[18] Diederik P Kingma and Jimmy Ba. Adam: A method for stochastic optimization. arXiv preprint arXiv:1412.6980, 2014.

The invention claimed is:

1. A computer implemented system for de novo sequencing of peptides from a sample mass spectrometry data using neural networks, the computer implemented system comprising:
   a processor and at least one memory providing a plurality of layered nodes configured to form an artificial neural network for generating a probability measure for one or more candidates to a next amino acid in an amino acid sequence, the artificial neural network trained on known mass spectrometry data representing theoretical fragment ions peaks of known sequences differing in length and differing by one or more amino acids;
   wherein the plurality of layered nodes comprise at least one node configured to receive:
      the sample mass spectrometry data comprising a plurality of coordinate data pairs representing m/z and intensity values of observed fragment ion peaks, and
      a second coordinate data representing the theoretical fragment ion peaks;
   wherein the plurality of layered nodes receives the sample mass spectrometry data as input, the plurality of layered nodes comprising:
      at least one convolutional and/or fully connected layer for comparing at least one of the observed fragment ion peak against at least one of the theoretical fragment ion peaks; and
   wherein the plurality of layered nodes is configured for:
      identifying the difference in m/z between the observed fragment ion peaks and the theoretical fragment ion peaks;
      identifying a matching theoretical fragment ion peak to the at least one observed fragment ion peak by constraining a difference tensor (D) representing the difference in m/z between the observed fragment ion peaks and the theoretical fragment ion peaks; and
      outputting an amino acid sequence corresponding to the at least one observed fragment ion peak; and
   the processor configured to:
      obtain an input prefix representing a determined amino acid sequence of the peptide,
      identify a next amino acid based on a candidate next amino acid having a greatest probability measure based on the output of the artificial neural network and the sample mass spectrometry data; and
      update the determined amino acid sequence with the next amino acid.

2. The system of claim 1, wherein the plurality of coordinate data pairs is a subset selected based on intensity.

3. The system of claim 1, wherein the difference tensor comprises a 3-dimensional tensor representing the difference in m/z between the observed fragment ion peaks and theoretical fragment ion peaks for each token and ion type pair.

4. The system of claim 1, wherein the plurality of layered nodes identifies the matching theoretical fragment ion peak by constraining the difference tensor according to equation 2:

$$\sigma(D) = \exp\{-|D|*c\} \quad (2)$$

wherein:
σ(D) is an activation function,
D is the difference tensor, and
c is a constant.

5. The system of claim 4, wherein c is between 70 and 120.

6. The system of claim 5, wherein c is about 100.

7. The system of claim 1, wherein the plurality of layered nodes comprise at least one convolutional layer for comparing the observed fragment ion peak against the theoretical fragment ion peak.

8. The system of claim 7, comprising three one-dimensional convolutional layers, a pooling layer, and three fully connected layers.

9. The system of claim 1, wherein the artificial neural network is further trained on a database of known peptide sequences; and
wherein the plurality of layered nodes comprise:
one or more layers comprising a first neural network for identifying amino acid sequences corresponding to the observed fragment ion peaks and generating one or more output vectors representing the amino acid sequences; and
one or more layers comprising a recurrent neural network (RNN) for predicting the next amino acid by vector embedding the one or more output vectors, and for outputting the probability measure for each candidate next amino acid.

10. The system of claim 9, wherein the one or more layers comprising the first neural network is trained with T Net™.

11. The system of claim 9, wherein the one or more layers of the plurality of layered nodes comprising the RNN is a long short-term memory network (LSTM).

12. The system of claim 11, wherein the LSTM is initialized with an embedding matrix to represent the sample mass spectrometry data.

13. The system of claim 12, wherein the represented spectrum data is computed by equation 4:

$$S = \sum_{i=1}^{N} I_i E_i \quad (4)$$

wherein:
S is the represented spectrum data,
N is the number of data pairs representing m/z and intensity values of fragment ion peaks,
I is intensity, and
E is positional embedding for m/z.

14. The system of claim 1, comprising a mass spectrometer configured to generate a sample mass spectrometry data of a peptide.

15. The system of claim 1, wherein the second coordinate data comprises data pairs representing m/z and intensity values of the theoretical fragment ion peaks.

16. The system of claim 1, wherein the plurality of layered nodes comprise at least one fully-connected layer for identifying:
a) a fragment ion peak corresponding to a sequence that is one amino acid longer than the determined amino acid sequence,
by fitting a plurality of candidates to a) against the sample mass spectrometry data, and for outputting the probability measure for each corresponding candidate next amino acid.

17. A method for de novo sequencing of peptides from mass spectrometry data using a plurality of layered nodes configured to form an artificial neural network for generating a probability measure for one or more candidates to a next amino acid in an amino acid sequence, the method comprising:
receiving, by at least one node of the plurality of layered nodes, a sample mass spectrometry data of a sample peptide, the sample mass spectrometry data comprising a plurality of coordinate data pairs representing m/z and intensity values of observed fragment ion peaks;
receiving, by the at least one node, a second coordinate data representing theoretical fragment ion peaks;
comparing at least one of the observed fragment ion peak against at least one of the theoretical fragment ion peaks by at least one convolutional and/or fully connected layer of the plurality of layered nodes, the plurality of layered nodes configured to:
identify the difference in m/z between the observed fragment ion peaks and the theoretical fragment ion peaks;
identify a matching theoretical fragment ion peak to the at least one observed fragment ion peak by constraining a difference tensor (D) representing the difference in m/z between the observed fragment ion peaks and the theoretical fragment ion peaks; and
output an amino acid sequence corresponding to the at least one observed fragment ion peak;
obtaining an input prefix representing a determined amino acid sequence of the sample peptide;
outputting a probability measure for each candidate of a next amino acid;
identifying a next amino acid based on a candidate next amino acid having a greatest probability measure based on the output of the artificial neural network and the sample mass spectrometry data; and
updating the determined amino acid sequence with the next amino acid.

18. The method of claim 17, comprising selecting a subset of the sample mass spectrometry data based on intensity, to generate the plurality of coordinate data pairs.

19. The method of claim 17, wherein the difference tensor comprises a 3-dimensional tensor representing the difference in m/z between the observed fragment ion peaks and theoretical fragment ion peaks for each token and ion type pair.

20. The method of claim 17, comprising identifies identifying the matching theoretical fragment ion peak by constraining the difference tensor according to equation 2:

$$\sigma(D) = \exp\{-|D|*c\} \quad (2)$$

wherein:
σ(D) is an activation function,
D is the difference tensor, and
c is a constant.

21. The method of claim 20, wherein c is between 70 and 120.

22. The method of claim 21, wherein c is about 100.

23. The method of claim 17, comprising:
   training the artificial neural network on a database of known peptide sequences;
   identifying amino acid sequences corresponding to the observed fragment ion peaks by one or more layers of the plurality of layered nodes comprising a first neural network;
   generating one or more output vectors representing a the amino acids sequences;
   predicting a next amino acid by vector embedding the one or more output vectors by one or more layers of the plurality of layered nodes comprising a recurrent neural network (RNN).

24. The method of claim 23, wherein the RNN is a long short-term memory network (LSTM), and wherein the method comprises initializing the LSTM with an embedding matrix to represent the sample mass spectrometry data.

25. The method of claim 24, wherein the represented spectrum data is computed by equation 4:

$$S = \sum_{i=1}^{N} I_i E_i \qquad (4)$$

wherein:
S is the represented spectrum data,
N is the number of data pairs representing m/z and intensity values of fragment ion peaks,
I is intensity, and
E is positional embedding for m/z.

26. The method of claim 17, comprising fitting a plurality of candidates to:
   a) a fragment ion peak corresponding to a sequence that is one amino acid longer than the determined amino acid sequence
against the sample mass spectrometry data to output the probability measure for each corresponding candidate next amino acid.

* * * * *